United States Patent
Piantoni et al.

(10) Patent No.: US 9,999,550 B2
(45) Date of Patent: Jun. 19, 2018

(54) MACHINE FOR MAKING ABSORBENT SANITARY ARTICLES

(71) Applicant: GDM S.p.A., Bologna (IT)

(72) Inventors: Matteo Piantoni, Albino (IT); Alberto Perego, Milan (IT)

(73) Assignee: GDM S.P.A., Bologna (IT)

(*) Notice: Subject to any disclaimer, the term of this patent is extended or adjusted under 35 U.S.C. 154(b) by 85 days.

(21) Appl. No.: 14/428,528

(22) PCT Filed: Oct. 11, 2013

(86) PCT No.: PCT/IB2013/059321
§ 371 (c)(1),
(2) Date: Mar. 17, 2015

(87) PCT Pub. No.: WO2014/060923
PCT Pub. Date: Apr. 24, 2014

(65) Prior Publication Data
US 2015/0272786 A1    Oct. 1, 2015

(30) Foreign Application Priority Data

Oct. 15, 2012 (IT) .............................. BO2012A0562

(51) Int. Cl.
*A61F 13/15* (2006.01)

(52) U.S. Cl.
CPC .. *A61F 13/15764* (2013.01); *A61F 13/15674* (2013.01); *A61F 13/15723* (2013.01)

(58) Field of Classification Search
CPC .......... A61F 13/15764; A61F 13/15674; A61F 13/15723; Y10T 156/1062; Y10T 156/1077; Y10T 156/1089
See application file for complete search history.

(56) References Cited

U.S. PATENT DOCUMENTS 6,074,333 A * 6/2000 Rajala ............... A61F 13/15756
493/346
9,011,626 B2 4/2015 Ito et al.
(Continued)

FOREIGN PATENT DOCUMENTS

| CN | 101803979 A | 8/2010 |
| CN | 101822591 A | 9/2010 |
| DE | 4335919 | 4/1995 |

OTHER PUBLICATIONS

Office Action issued by the State Intellectual Property Office of the People's Republic of China dated Jul. 21, 2016 for counterpart Chinese Application No. 201380053865.8.
(Continued)

*Primary Examiner* — Mark A Osele
*Assistant Examiner* — Christopher C Caillouet
(74) *Attorney, Agent, or Firm* — Shuttleworth & Ingersoll, PLC; Timothy J. Klima

(57) ABSTRACT

The machine according to the invention, for making absorbent sanitary articles, comprises a device for forming inside the absorbent article a pad composed of a plurality of superposed layers of absorbent material, a transfer roller located downstream of the device and having a cylindrical lateral surface, and a wrapping unit which is located downstream of the transfer roller and by which the pad is placed between a first sheet of impermeable or permeable material and a second sheet of permeable material; the transfer roller transfers the internal pad from the forming device to the wrapping unit, the forming device also comprises, for each layer of absorbent material, a respective forming unit for cutting into lengths a continuous web of absorbent material fed into the selfsame unit and for transferring the lengths to the transfer roller; the lengths of material fed by each unit (Continued)

are mutually superposed on the lateral surface of the transfer roller so as to form the layers of the pad and the pad itself.

12 Claims, 3 Drawing Sheets

(56) References Cited

U.S. PATENT DOCUMENTS

| | | | | |
|---|---|---|---|---|
| 2003/0150551 A1* | 8/2003 | Baker | ............... | A61F 13/15626 |
| | | | | 156/265 |
| 2012/0145314 A1* | 6/2012 | Piantoni | ............ | A61F 13/15764 |
| | | | | 156/256 |
| 2012/0247661 A1* | 10/2012 | Ogasawara | ....... | A61F 13/15723 |
| | | | | 156/256 |

OTHER PUBLICATIONS

International Search Report dated Mar. 10, 2014 for counterpart application No. PCT/IB2013/059321.

* cited by examiner

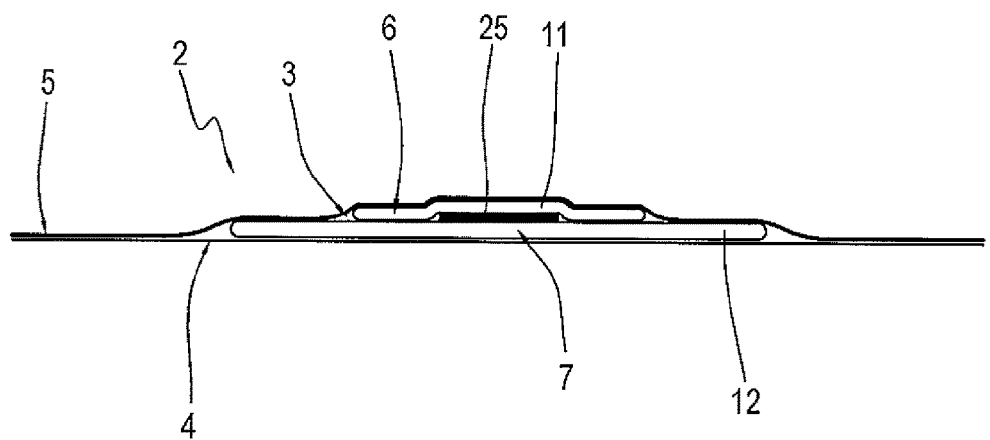
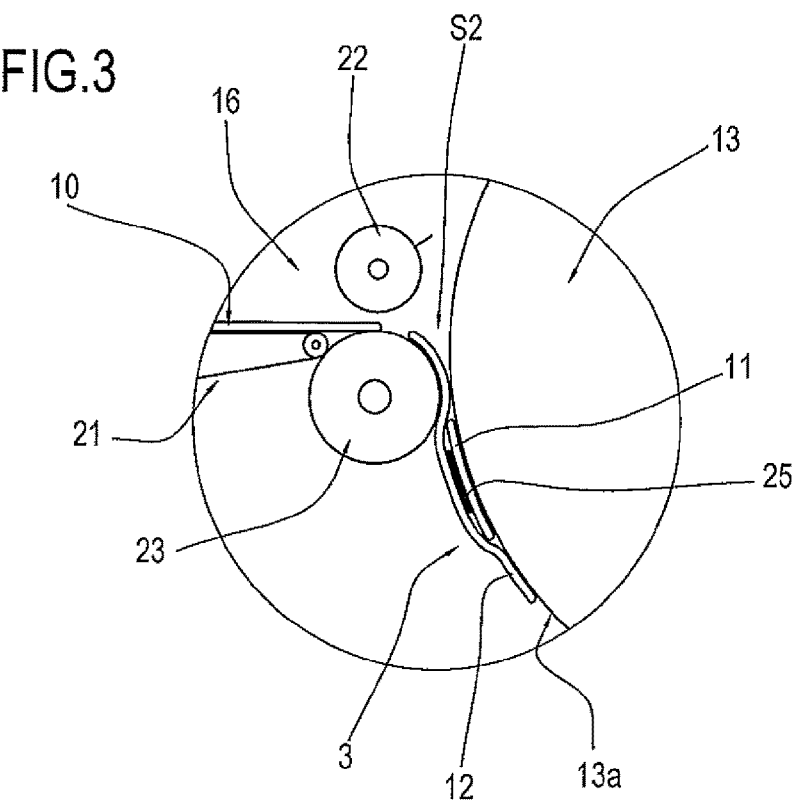

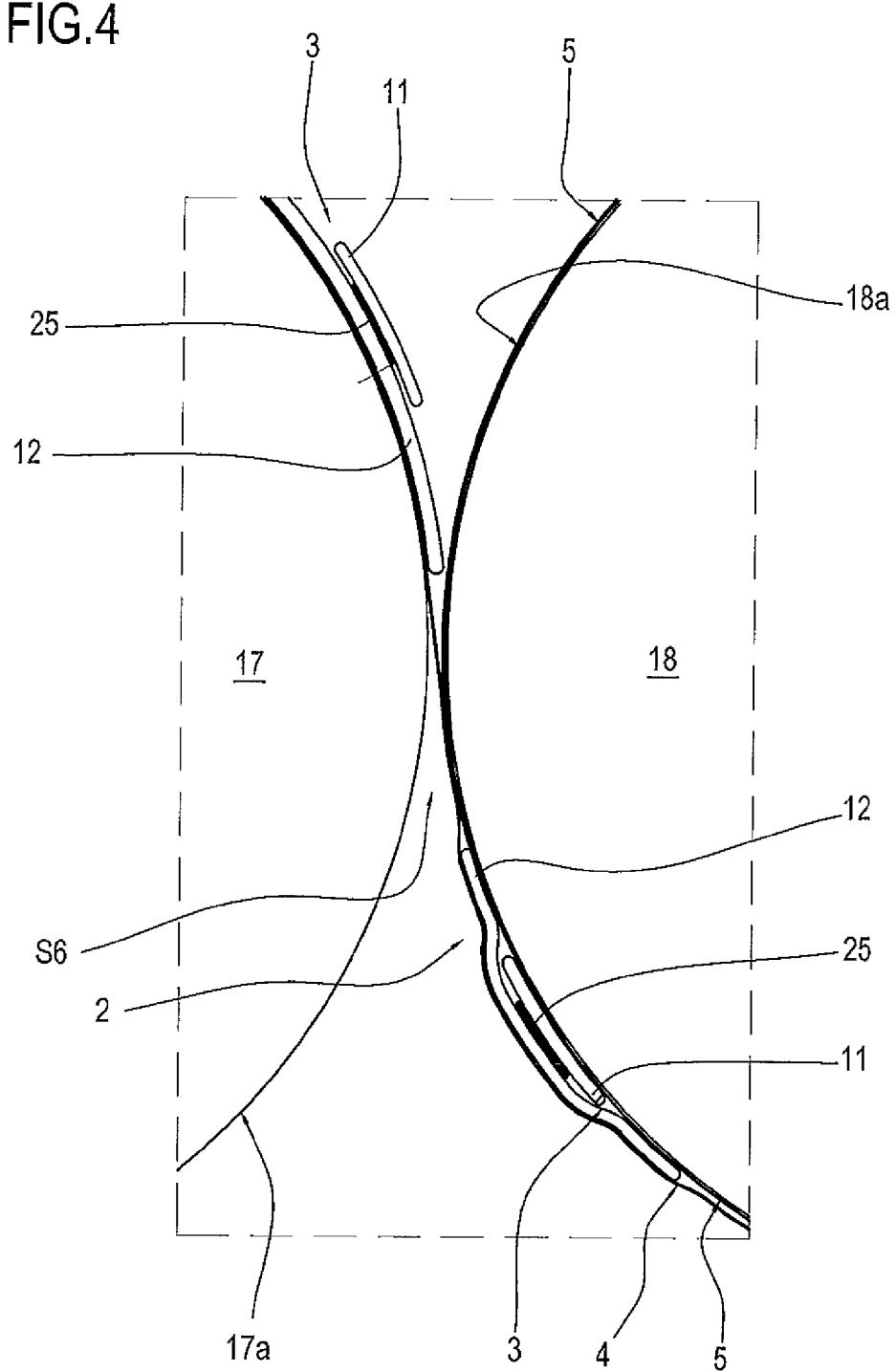

US 9,999,550 B2

MACHINE FOR MAKING ABSORBENT SANITARY ARTICLES

This application is the National Phase of International Application PCT/IB2013/059321 filed Oct. 11, 2013 which designated the U.S. and that International Application was published under PCT Article 21(2) in English.

This application claims priority to Italian Patent Application No. BO2012A000562 filed Oct. 15, 2012, which application is incorporated by reference herein.

TECHNICAL FIELD

This invention relates to a machine for making absorbent sanitary articles.

More precisely, the invention addresses the field of machines for making absorbent sanitary articles such as nappies for children. nappies for adults, ladies' sanitary towels and the like.

BACKGROUND ART

These absorbent articles comprise a pad composed of at least two layers of absorbent material which are superposed in order to increase the absorbent capacity of the article.

To obtain the internal absorbent pad, prior art machines superpose on a first continuous layer of absorbent material one or more further layers of absorbent material.

Once the layers have been superposed, the pads thus obtained are still joined to each other and it is therefore necessary to divide them into single pads before wrapping them between a sheet of permeable non-woven fabric, known as "topsheet", and a sheet of impermeable material, known as "backsheet", thus obtaining a continuous row of finished articles.

The main problem of the prior art machines regards their structural and kinematic complexity.

Indeed, they perform numerous operations on the product being made, which means the product undergoes numerous steps before it is completed.

To be able to perform all the operations needed to make the article, the machine must be equipped with a large number of devices and components.

That means the machine is necessarily very complex in both structural and kinematic terms because all the devices and components have to be precisely co-ordinated.

It follows that the complexity and large number of operations are reflected also in the total amount of time required to make the finished article.

DISCLOSURE OF THE INVENTION

This invention has for an aim to provide a machine for making absorbent sanitary articles which overcomes the above mentioned disadvantages of the prior art.

More specifically, the main aim of the invention is to provide a machine for making absorbent sanitary articles which is not complex in construction and whose operation is simpler than that of prior art machines.

This aim is fully achieved by a machine for making absorbent sanitary articles having the features set forth herein.

Further advantageous aspects of the machine are set forth in the present disclosure.

BRIEF DESCRIPTION OF THE DRAWINGS

This and other features of the invention will become more apparent from the following description of a preferred embodiment of it, illustrated by way of non-limiting example in the accompanying drawings, in which:

FIG. 2 shows a sectional side view of an absorbent article according to the invention;

FIG. 3 is an enlarged side view of a first detail from FIG. 1;

FIG. 4 is an enlarged side view of a second detail from FIG. 1.

DETAILED DESCRIPTION OF PREFERRED EMBODIMENTS OF THE INVENTION

Figure 1:
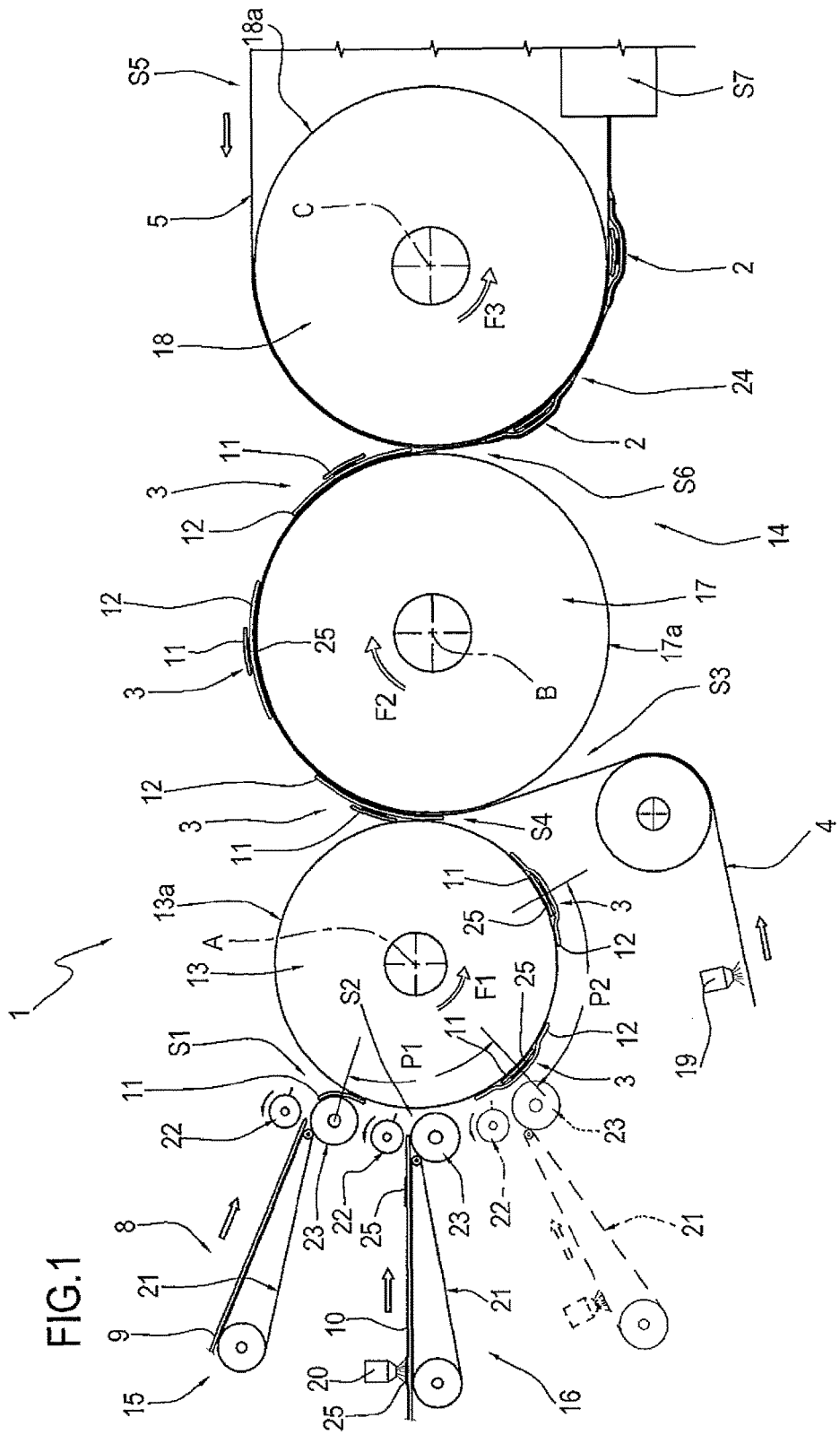
FIG. 1 shows a side view of a machine according to the invention.

With reference to FIG. 1, the numeral 1 denotes in its entirety a machine for making absorbent sanitary articles 2 according to this invention.

As shown in detail in FIG. 2, the absorbent article 2 comprises an internal absorbent pad 3 which is composed of two or more layers of absorbent material and is wrapped between a first sheet 4 of impermeable material, defining what is known in the jargon of the trade as the "backsheet" of the absorbent article 2, and a second sheet 5 of permeable material, defining what is known in the jargon of the trade as the "topsheet" of the absorbent article 2. In another embodiment, the pad 3 might be wrapped between a first sheet 4 and a second sheet 5 which are both made of permeable material.

The article 2, made by the machine shown in FIG. 1, has an internal pad 3 which is composed of a first layer 6 and a second layer 7 of absorbent material.

It should be noted that the internal pad 3 may also comprise more than two layers and also that the layers may be made of the same material or one or more of the layers may be made of a material different from the other layers.

As shown in FIG. 1, the machine 1 comprises a device 8 for forming the internal pad 3.

More precisely, each layer 6,7 of the pad 3 is obtained from a respective continuous web 9,10 of absorbent material and, according to the invention, the forming device 8 receives as many continuous webs of absorbent material as there are layers making up the internal pad 3.

According to a preferred embodiment of it, the machine 1 makes an absorbent article 2 comprising a pad 3 which is composed of two layers of absorbent material and thus the forming device 8 receives a first continuous web 9 and a second continuous web 10 of absorbent material, each of which is processed by the device 8 itself to form the first layer 6 and the second layer 7 of the pad 3, respectively.

More precisely, as will become clearer as this description continues, the forming device 8 cuts the first web 9 and the second web 10 into first lengths 11 and second lengths 12, respectively, which are mutually superposed to form the layers 6 and 7 of the pad 3 and the pad 3 itself.

Downstream of the forming device 8, the machine 1 further comprises a roller 13, with a cylindrical lateral surface 13a, for transferring the pads 3 and a wrapping unit 14 for the pads 3 which is located downstream of the transfer roller 13 and by which each pad 3 is placed between the first sheet 4 of impermeable material and the second sheet 5 of permeable material to obtain the finished absorbent article 2.

The roller 13 transfers the pads 3 from the forming device 8 to the wrapping unit 14.

The forming device 8 comprises, for each layer 6,7 of absorbent material making up the pad 3, a respective forming unit 15,16 for cutting into lengths 11,12 the continuous webs 9,10 of absorbent material fed into the selfsame unit and for transferring the lengths 11,12 to the transfer roller 13. The lengths 11,12 of material fed by each forming unit 15,16 are mutually superposed on the lateral surface 13a of the transfer roller 13 so as to form the layers 6,7 of the pad 3 and the pad 3 itself.

In particular in the preferred embodiment, the transfer roller 13 receives the first lengths 11 at a first station S1 and the second lengths 12 at a second station S2 located downstream of the first station S1 in the direction of rotation of the roller 13 indicated by the arrow F1.

At the second station S2, shown better in FIG. 3, each second length 12 is superposed over a respective first length 11, thereby forming the internal pad 3.

The cylindrical lateral surface 13a of the transfer roller 13 is provided with a plurality of holes (not illustrated) which are used to hold the pad 3 down by suction while it is being transferred to the wrapping unit 14.

The wrapping unit 14 comprises a first assembly roller 17, located downstream of the transfer roller 13 and which receives the first sheet 4 of permeable material at a third station S3.

At a fourth station S4, located downstream of the third station S3 in the direction of rotation of the first assembly roller 17 indicated by the arrow F2, the first assembly roller 17 also receives the internal pad 3 which is placed on the first sheet 4 during transfer from the transfer roller 13 to the first assembly roller 17.

More in detail, the first sheet 4 has a glued side and the internal pad 3 is transferred and placed on this glued side in such a way that the internal pad 3 can adhere to the first sheet 4, thus facilitating transfer of the pad 3 by the first roller 17.

Gluing is accomplished by a first gluing device of known type, labelled 19 in the drawing, located upstream of the third station S3.

It should be noted that the first gluing device 19 might be located downstream of, or directly at, the third station S3.

The first assembly roller 17 also has a cylindrical lateral surface 17a which is substantially tangent to the lateral surface 13a of the transfer roller 13. This guarantees and improves the adherence of the pad 3 to the first sheet 4 during transfer from one roller to the other.

The first assembly roller 17 also has a cylindrical lateral surface 17a which is provided with suction holes (not illustrated) used to make the first sheet 4 adhere properly to the surface 17a itself and to hold the pad 3 down while it is being transferred.

The wrapping unit 14 also comprises a second assembly roller 18, which is located downstream of the first assembly roller 17 and which receives the second sheet 5 of permeable material at a fifth station S5.

At a sixth station S6, shown in more detail in FIG. 4, located downstream of the fifth station S5 in the direction of rotation of the second assembly roller 18, indicated by the arrow F3, the second roller 18 receives from the first roller 17, the internal pad 3 adhering to the first sheet 4 of impermeable material.

The second roller 18 has a cylindrical lateral surface 18a, which is substantially tangent to the lateral surface 17a of the first assembly roller 17. Thus, the second sheet 5, too, is made to adhere to the first sheet 4 and to the pad 3 during their transfer from the first roller to the second roller 18.

The lateral surface 18a also has suction holes (not illustrated) to make the second sheet 5 adhere properly to the roller 18 and to hold down the pad 3 wrapped between the two sheets 4,5 while it is being conveyed towards a seventh station S7 where it is fed out of the machine 1.

The glue applied to the first sheet 4 allows also the second sheet 5 to adhere to it, thereby causing the sheets 4,5 to form a complete and adherent wrapping round the pad 3.

The forming device 8 comprises a first forming unit 15 whereby the first continuous web 9 of absorbent material is cut into the first lengths 11 and the first lengths 11 are conveyed to the transfer roller 13, and a second forming unit 16 whereby the second continuous web 10 of absorbent material is cut into the second lengths 12 and the second lengths 12 are conveyed to the transfer roller 13.

Since the pad 3 might also have more than two layers, it follows that the forming device 8 might accordingly comprise more than two forming units for cutting and transferring the respective lengths of absorbent material.

The dashed lines in FIG. 1 represent a further forming unit for cutting and transferring a third length of absorbent material, not illustrated.

According to the invention, each unit of the forming device 8 feeds the cut lengths to the transfer roller 13 spaced from each other at a predetermined, preset spacing.

More precisely, each forming unit located downstream of the first unit 15 feeds the lengths of absorbent material to the transfer roller 13 spaced from each other at a respective spacing in phase with at least one of the spacings defined by the forming units located upstream of that unit. Preferably, the spacings defined by the units downstream of the first unit 15 are respectively in phase with the spacing defined by the selfsame first unit 15.

The difference in spacing of the lengths at the respective spacing is obtained by an acceleration imparted to the selfsame lengths of absorbent material cut by each unit before being fed to the transfer roller 13.

As further illustrated in FIG. 1, the first unit 15 comprises a conveyor 21, of known type, for feeding the first continuous web 9 towards an element 22, also of known type, for cutting the first web 9 into the first lengths 11. Further, to achieve the aforementioned acceleration, the first unit 15 comprises an accelerator roller 23, of known type, located between the conveyor 21 and the transfer roller 13 and capable of accelerating the first cut lengths 11 and transferring them onto the lateral surface 13a of the transfer roller 13 spaced from each other at a first predetermined, preset spacing p1.

Similarly, the second unit 16 comprises a conveyor 21, of known type, for feeding the second continuous web 10 towards an element 22, of known type, for cutting the second web 10 into the second lengths 12. The second unit 16, too, comprises an accelerator roller 23, of known type, located between the conveyor 21 and the transfer roller 13 and capable of accelerating the second cut lengths 12 and transferring them onto the lateral surface 13a of the transfer roller 13 spaced from each other at a second predetermined, preset spacing p2 in phase with the first spacing p1.

Preferably, the elements 22 of each unit 15,16 act in conjunction with the respective accelerator rollers 23 to cut the web 9 and the web 10.

More specifically, in order to allow the lengths of absorbent material to be correctly superposed at the second station S2, the value of the first spacing p1 at which the first lengths 11 are fed to the transfer roller 13 is the same as the value of the second spacing p2 at which the second lengths 12 are fed to the transfer roller 13. For reasons described in more detail below, on the other hand, the phase between them may vary.

It will be understood, however, that as described and illustrated, the value of the first spacing p1, or of the second spacing p2, is such that after the lengths 11 and 12 have been superposed, the pads 3 are equispaced on the lateral surface 13a of the transfer roller 13.

Advantageously, the first unit 15 and the second unit 16 of the forming device 8 comprise the same components just described.

In other words, it is possible and advantageous for the machine 1 to be equipped with identical units for forming each layer of the pad 3.

Thus, the machine 1 is structurally simple and the use of identical components allows simplifying the kinematic coordination between the units so that the respective spacings obtained are suitable for correctly superposing the lengths of absorbent material, thereby saving on installation and maintenance costs.

Moreover, a precise phase is defined between the first spacing p1 and the second spacing p2, or more generally speaking, between the spacing defined by a unit downstream relative to at least one of the spacings defined by the units upstream, so as to position the lengths precisely relative to each other. In other words, the position at which one length is superposed on the preceding ones may vary in order to locate at different positions the more absorbent zones of the absorbent article 2.

For example, this concept applies to the case where an absorbent article 2 for males instead of an absorbent article 2 for females is to be made.

In effect, in an absorbent article 2 for males, the more absorbent zone must be located towards the front of the pad 3 and of the article 2 itself, whereas in an absorbent article 2 for females, the more absorbent zone must be located more centrally.

In the case illustrated in the accompanying drawings, the first length 11 is located at a central position relative to the second length 12 and relative to the pad 3 and hence, the phase between the first spacing p1 and the second spacing p2 is zero.

The adoption of the aforementioned units, with the components described, allows a machine 1 to be provided which lends itself to the production of different types and categories of absorbent products while maintaining its reduced structural complexity and without increasing the complexity of the kinematic coordination between the units.

Furthermore, to keep the first length 11 and the second length 12 of absorbent material together after they have been superposed, preventing them from becoming separated while they are being conveyed on the lateral surface 13a of the transfer roller 13, the machine 1 comprises a second gluing device 20, also of known type.

The second gluing device 20 applies a layer of glue 25 on one side of the second web 10. This side corresponds to the side of the second cut length 12 which substantially comes into contact with the first length 11 during superposition.

Preferably, the second gluing device 20 is located upstream of the second forming unit 16. Also, the second gluing device 20 may be located upstream of the cutting element 22 or downstream of it in order to apply the layer of glue 25 directly on the second cut length 12.

Further, the second gluing device 20 applies the layer of glue 25 intermittently and in phase with the spacing p1.

The glue is applied in phase with the spacing p1 so that when the lengths 11,12 are superposed, the layer of glue 25 is placed precisely at the length 11, thus guaranteeing that they adhere to each other correctly.

In more general terms, in the case where the machine 1 comprises more than two forming units, it is preferable for each forming unit located downstream of the first unit 15 to be equipped with a gluing device of its own. Each gluing device applies glue on the respective web intermittently and in phase with at least one of the forming units located upstream. More specifically, the second gluing device 20 applies the layer of glue 25 in phase with at least one of the spacings defined by the forming units located upstream, so that each length can be made to adhere correctly as one with those preceding it.

In use, the machine 1 receives the first web 9 and the second web 10 of absorbent material.

The first web 9 is fed to the first unit 15 of the forming device 8, while the second web 10 is fed to the second unit 16 of the selfsame device 8.

The first web 9 is fed by the conveyor 21 of the first unit 15 towards the cutting element 22, which divides the web 9 into the first lengths 11 of absorbent material.

The feed motion of the first cut lengths 11 is then speeded up by an accelerator roller 23 and the first lengths 11 are transferred onto the cylindrical lateral surface 13a of the transfer roller 13 at a predetermined, preset spacing p1.

Similarly, the second web 10 is fed towards the cutting element 22 of the second unit 16 through the agency of its conveyor 21 and is divided into the second lengths 12, which are accelerated by the accelerator roller 23 and transferred onto the cylindrical lateral surface 13a of the transfer roller 13 at a spacing p2 equal to and in phase with the first spacing p1.

The transfer roller 13 rotates at constant speed about its axis A in anticlockwise direction in the representation of the machine 1 in FIG. 1. The accelerator rollers 23 of the first and second units 15 and 16, on the other hand, rotate in clockwise direction in the example of FIG. 1.

More specifically, the transfer roller 13 receives the first lengths 11 at the first station S11 and the second lengths 12 at the second station S2, downstream of the first in the direction of rotation of the roller 13 itself.

Before placing the second length 12 on the transfer roller 13, at the second station S2, the second unit 16 causes glue to be applied intermittently and in phase with the spacing p1 of the second web 10, so that the second length 12 is held down on and made to adhere to the first length 11, preventing the two from being separated and making it easier for the transfer roller 13 to transport the internal pad 3 thus made.

More in detail, the correct and desired superposition of the lengths of absorbent material, at a second spacing p2 equal to the first spacing p1 and with the desired phase between them, is obtained by suitably setting both the speed at which the webs 9 and 10 are fed by the respective conveyors 21 and the acceleration phases imparted by the respective accelerator rollers 23.

Further, the setting of the feed speed of the webs 9 and 10 and the setting of the acceleration phases imparted by the respective accelerator rollers 23 to cut lengths 11 and 12 also take into account the different dimensions of the lengths 11 and 12.

In the embodiment illustrated, the first lengths 11 are shorter than the second lengths 12, which means that the cut-to-cut spacing for the first lengths 11 is smaller than the cut-to-cut spacing for the second lengths 12.

The settings therefore take into account not only the phase that is required between the first spacing p1 and the second spacing p2 but also the fact that difference in spacing which the first lengths 11 undergo as they are brought from the value of the cut-to-cut spacing to the first spacing p1 is greater than the difference in spacing which the second lengths 12 undergo as they are brought from the value of the cut-to-cut spacing to the second spacing p2, which is equal to the first spacing p1.

More specifically, in the embodiment of the pad 3 illustrated, where the first length 11, which is shorter than the second length 12, is located at a central position in the pad 3, the accelerator rollers 23 of the first and second units 15 and 16 are co-ordinated in such a way that the phase displacement between the first spacing p1 and the second spacing p2 is zero.

To obtain a pad 3 where the first length 11, after superposition, is located more towards the front portion or the rear portion of the pad 3, the accelerator rollers 23 of the first and second units 15 and 16 can be co-ordinated with each other in such a way as to define the desired phase displacement of the second spacing p2 relative to the first spacing p1 by delaying or advancing the transfer of the second length 12 on the transfer roller 13.

Also, preferably, the settings of the feed speed of the webs 9 and 10 and the acceleration phases imparted to the cut lengths 11 and 12 by the respective accelerator rollers 23 should be such that, when the lengths 11 and 12 are superposed, a pad 3 is obtained in which the first length 11 is entirely contained in the space occupied by the second length 12.

It is also preferable for the application of the layer of glue 25 to take into account the dimensions and relative position of the lengths 11 and 12.

In effect, it is preferable for the layer of glue 25 to be shorter than the shorter length, in this case the first length 11, so that when the two lengths are superposed, the layer of glue 25 is entirely within the space occupied by the shorter length, thereby preventing glue from being smeared beyond the edges of the shorter length itself. It is also preferable for the application of the layer of glue 25 to take into account the relative position between the first length 11 and the second 12 and hence the phase displacement required between the first spacing p1 and the second spacing p2.

The transfer roller 13 transfers the pad 3 to the first assembly roller 17 while holding the pad 3 down on its lateral surface 13a thanks to the suction holes it is provided with.

The first assembly roller 17 rotates at constant speed about its axis B in clockwise direction in the representation in FIG. 1.

The first roller 17 receives the first sheet 4 of permeable material at the third station S3. The lateral surface 17a of the first roller 17, thanks to the suction holes also on it, holds down the first sheet 4.

At the fourth station S4, located downstream of the third station S3 in the direction of rotation of the first assembly roller 17, the lateral surface 13a of the transfer roller 13 and the lateral surface 17a of the first assembly roller 17 are substantially tangent and their peripheral speeds concordant.

At the fourth station S4, the pad 3 is placed on the first sheet 4 of impermeable material.

To better guarantee adherence between the pad 3 and the first sheet 4, the latter is glued on the side of it which will be placed in contact with the pad 3.

Gluing is accomplished by the first gluing device 19 which, in the representation of the machine 1 in FIG. 1, is located upstream of the third station S3.

Once the pad 3 has been transferred and made to adhere to the first sheet 4, the first assembly roller 17 conveys the group thus obtained towards a second assembly roller 18. As illustrated, the second assembly roller 18 rotates at constant speed about its axis C in anticlockwise direction.

At the fifth station S5, the second roller 18 receives the second sheet 5 of permeable material, which is held down on the lateral surface 18a of the second roller 18 thanks to the suction holes on that surface.

Transfer of the aforestated group from the first assembly roller 17 to the second 18 occurs at the sixth station S6 (FIG. 4), located downstream of the fifth station S5 in the direction of rotation of the second roller 18.

Further, at the sixth station S6, the lateral surfaces 17a and 18a of the first and second assembly rollers 17 and 18 are substantially tangent and their respective peripheral speeds concordant.

During transfer, the second sheet 5 is attached as one with and made to adhere to the pad 3 and to the first sheet 4 thanks to the glue on the first sheet 4.

Thus, downstream of the sixth station S6, a continuous row 24 of absorbent articles 2 is formed and held down on the roller 18 by the suction holes on the lateral surface 18a of the roller.

Lastly, the second assembly roller 18 transfers the continuous row 24 of absorbent articles 2 to the seventh station S7 which feeds the continuous row 24 out of the machine 1 towards further processing stations such as, for example, a station where the continuous row 24 is cut into individual absorbent articles 2.

The machine 1 as described brings numerous advantages.

First of all, the machine 1 as a whole has a simple structure.

In effect, with reference to the device 8 for forming the internal pad 3, the device 8 is defined by units for forming the layers 6 and 7 and which comprise components of substantially known type and, as described in the foregoing, structurally and functionally simple.

This allows the lengths 11,12 of absorbent material to be properly superposed without using complex control methods and devices.

In effect, superposing the lengths of absorbent material by spacing them according to predetermined, preset spacing values is a solution which is at once effective and easy to implement. Moreover, the adoption of accelerator rollers 23 of known type further simplifies this operation without complicating the structure of the machine 1 and makes the phasing of the spacings equally simple.

Moreover, directly superposing the cut lengths 11,12 allows single separate pads 3 to be obtained immediately. This allows saving on the number of components necessary for making the pad 3 and the finished absorbent article 2 because, for example, there is no need for the manufacturing process to have further steps for cutting the single pads.

Reducing the number of steps needed to complete the process of manufacturing the absorbent article 2 also means reducing the time needed to manufacture the finished absorbent article 2, thus increasing the overall productivity of the machine 1.

Another advantageous aspect of the machine 1 is the absence of waste material and offcuts when the webs of absorbent material are cut into lengths. In effect, each web of absorbent material is cut into lengths without any particular shape which allows considerable economic savings because there are no offcuts or wasted absorbent material of any kind.

Also, the use of forming units 15,16 having identical components allows further savings on the components used and maintenance costs because the types of components to be replaced are fewer in number.

Moreover, as stated and stressed several times in the foregoing description, the machine 1 according to the invention is capable of making different types of absorbent articles 2, for both male and female users or having a pad 3 which is composed of more than two layers of absorbent material.

The invention described above is susceptible of industrial application and may be modified and adapted in several ways without thereby departing from the scope of the inventive concept. Moreover, all the details of the invention may be substituted for technically equivalent elements.

The invention claimed is:

1. A machine for making an absorbent sanitary article, comprising:
    a forming device for forming a pad for placement inside the absorbent sanitary article, the pad being composed of a plurality of superposed layers of absorbent material,
    a transfer roller located downstream of the forming device and having a cylindrical lateral surface, and
    a wrapping unit by which the pad is placed between a first sheet of impermeable or permeable material and a second sheet of permeable material;
    the transfer roller transferring the internal pad from the forming device to the wrapping unit,
    the forming device comprising, for each layer of absorbent material, a respective forming unit for cutting into cut lengths a continuous web of absorbent material fed into the forming unit and for transferring the cut lengths to the transfer roller; the cut lengths of absorbent material fed by each forming unit being mutually superposed on the cylindrical lateral surface of the transfer roller to form the layers of the pad and the pad, the pad being completely constructed on the transfer roller and then directly transferred to the wrapping unit, the placement of the pad between the first sheet of impermeable or permeable material and the second sheet of permeable material beginning only upon transfer of the pad to the wrapping unit.

2. The machine according to claim 1, wherein each forming unit of the forming device feeds the cut lengths to the transfer roller spaced from each other at a predetermined, pre-set spacing; each forming unit that is located downstream of a first forming unit feeding the cut lengths to the transfer roller spaced from each other at a respective spacing in phase with at least one of the spacings defined by the first forming unit.

3. The machine according to claim 2, wherein the spacing of the cut lengths at the respective spacing is obtained by an acceleration imparted to the lengths of each unit before being fed to the transfer roller.

4. The machine according to claim 3, wherein each forming unit of the forming device comprises
    a conveyor for feeding the continuous web into the forming unit,
    an element for cutting the continuous web into the cut lengths,
    an accelerator roller located between the conveyor and the transfer roller for accelerating the cut lengths and transferring the cut lengths to the transfer roller spaced from each other at the predetermined, pre-set spacing.

5. The machine according to claim 4, and further comprising, for each forming unit located downstream of the first forming unit, a gluing unit for intermittently applying, in phase with at least one of the forming units located upstream, a layer of glue on one side of the continuous web being fed into the forming unit or on the cut length, a side for contact with at least one of the cut lengths fed by the forming units located upstream.

6. The machine according to claim 1, wherein the pad includes two superposed layers of absorbent material and the forming device comprises:
    a first forming unit for cutting into first lengths a first continuous web of absorbent material fed into the first forming unit and for transferring the first lengths to the transfer roller spaced from each other at a predetermined, pre-set first spacing p1,
    a second forming unit for cutting into second lengths a second continuous web of absorbent material fed into the second forming unit and for transferring the second lengths to the transfer roller spaced from each other at a predetermined, pre-set second spacing p2 and in phase with the first spacing p1.

7. The machine according to claim 6, wherein the wrapping unit comprises:
    a first assembly roller, located downstream of the transfer roller, which receives the first sheet of impermeable or permeable material, glued on one side, and
    a second assembly roller, located downstream of the first assembly roller, which receives the second sheet of permeable material;
    the internal pad being placed on the glued side of the first sheet during transfer from the transfer roller to the first assembly roller and the second sheet being wrapped on the pad and on the first web of impermeable material during transfer of the pad and of the first web from the first assembly roller to the second assembly roller.

8. The machine according to claim 1, wherein each forming unit of the forming device comprises:
    a conveyor for feeding the continuous web into the forming unit,
    an element for cutting the continuous web into the cut lengths,
    an accelerator roller located between the conveyor and the transfer roller for accelerating the cut lengths and transferring the cut lengths to the transfer roller spaced from each other at the predetermined, pre-set spacing.

9. The machine according to claim 8, and further comprising, for each forming unit located downstream of the first forming unit, a gluing unit for intermittently applying, in phase with at least one of the forming units located upstream, a layer of glue on one side of the continuous web being fed into the forming unit or on the cut length, a side for contact with at least one of the cut lengths fed by the forming units located upstream.

10. The machine according to claim 9, wherein the wrapping unit comprises:
    a first assembly roller, located downstream of the transfer roller, which receives the first sheet of impermeable or permeable material, glued on one side, and
    a second assembly roller, located downstream of the first assembly roller, which receives the second sheet of permeable material;
    the internal pad being placed on the glued side of the first sheet during transfer from the transfer roller to the first assembly roller and the second sheet being wrapped on the pad and on the first web of impermeable material during transfer of the pad and of the first web from the first assembly roller to the second assembly roller.

11. The machine according to claim 8, wherein the wrapping unit comprises:
    a first assembly roller, located downstream of the transfer roller, which receives the first sheet of impermeable or permeable material, glued on one side, and a second assembly roller, located downstream of the first assembly roller, which receives the second sheet of permeable material;

the internal pad being placed on the glued side of the first sheet during transfer from the transfer roller to the first assembly roller and the second sheet being wrapped on the pad and on the first web of impermeable material during transfer of the pad and of the first web from the first assembly roller to the second assembly roller.

12. The machine according to claim 1, wherein the wrapping unit comprises:

a first assembly roller, located downstream of the transfer roller, which receives the first sheet of impermeable or permeable material, glued on one side, and a second assembly roller, located downstream of the first assembly roller, which receives the second sheet of permeable material;

the internal pad being placed on the glued side of the first sheet during transfer from the transfer roller to the first assembly roller and the second sheet being wrapped on the pad and on the first web of impermeable material during transfer of the pad and of the first web from the first assembly roller to the second assembly roller.

\* \* \* \* \*